United States Patent [19]

Raines

[11] Patent Number: 5,623,969
[45] Date of Patent: Apr. 29, 1997

[54] NORMALLY CLOSED ASPIRATION VALVE

[75] Inventor: Kenneth C. Raines, Bethlehem, Pa.

[73] Assignee: B. Braun Medical Inc., Allentown, Pa.

[21] Appl. No.: 479,332

[22] Filed: Jun. 7, 1995

[51] Int. Cl.⁶ .................................................. F16K 15/14
[52] U.S. Cl. ........................... 137/854; 604/411; 222/83
[58] Field of Search ............................... 137/851, 854; 604/247, 408, 411, 412, 413, 905; 222/83, 107

[56] References Cited

U.S. PATENT DOCUMENTS

| | | | |
|---|---|---|---|
| 4,210,173 | 7/1980 | Choksi et al. | 137/843 |
| 4,222,407 | 9/1980 | Ruschke et al. | 137/843 |
| 4,244,378 | 1/1981 | Brignola | 137/843 |
| 4,246,932 | 1/1981 | Raines | 137/512 |
| 4,274,445 | 6/1981 | Cooper . | |
| 4,310,017 | 1/1982 | Raines . | |
| 4,354,492 | 10/1982 | McPhee | 137/854 |
| 4,364,387 | 12/1982 | Larkin | 222/83 |
| 4,429,856 | 2/1984 | Jackson . | |
| 4,506,691 | 3/1985 | Tseo . | |
| 4,535,820 | 8/1985 | Raines | 137/854 X |
| 4,556,086 | 12/1985 | Raines | 137/852 |
| 4,610,276 | 9/1986 | Paradis et al. | 137/856 |
| 4,726,149 | 2/1988 | Pickl, Jr. | 137/843 |
| 4,765,372 | 8/1988 | Beecher | 137/843 |
| 4,898,581 | 2/1990 | Iwatschenko | 137/854 |
| 5,230,706 | 7/1993 | Duquette | 604/83 |
| 5,334,180 | 8/1994 | Adolf et al. | 604/905 |
| 5,391,150 | 2/1995 | Richmond | 604/111 |
| 5,405,333 | 4/1995 | Richmond | 604/408 X |
| 5,454,805 | 10/1995 | Brony | 604/406 |

*Primary Examiner*—Edward K. Look
*Assistant Examiner*—Michael S. Lee
*Attorney, Agent, or Firm*—Hopgood, Calimafde, Kalil & Judlowe L.L.P.

[57] ABSTRACT

A valve having two elements each with a respective passageway, with one of the elements having a support and the other element having a shoulder, and a disc mounted between the elements and partially flexed over the support to form a seal on the shoulder preventing flow between the passageways until a relative pressure differential between the passageways fully flexes the disc over the support to allow flow between the passageways.

17 Claims, 4 Drawing Sheets

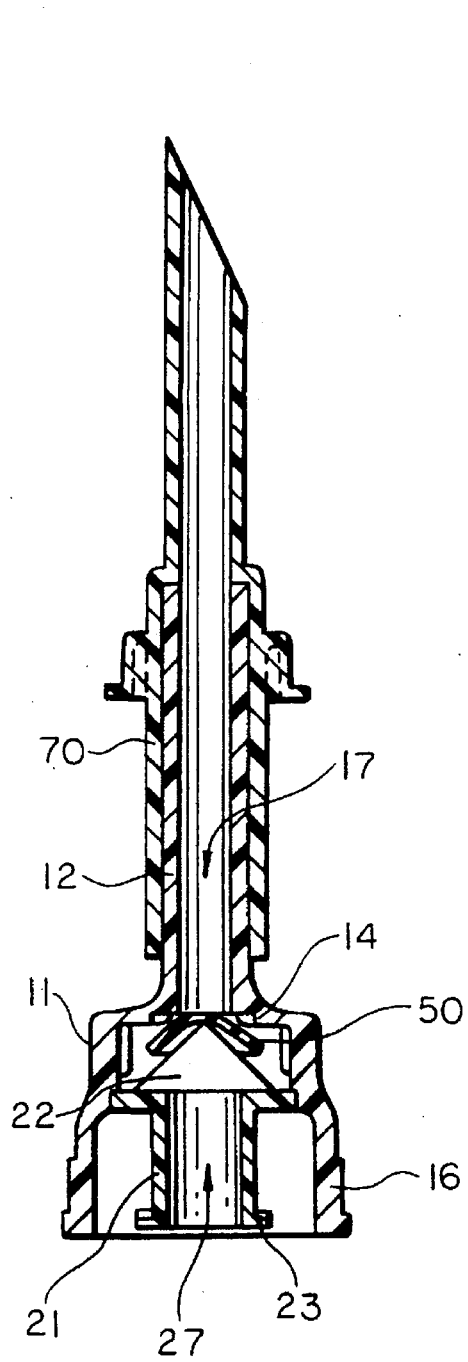
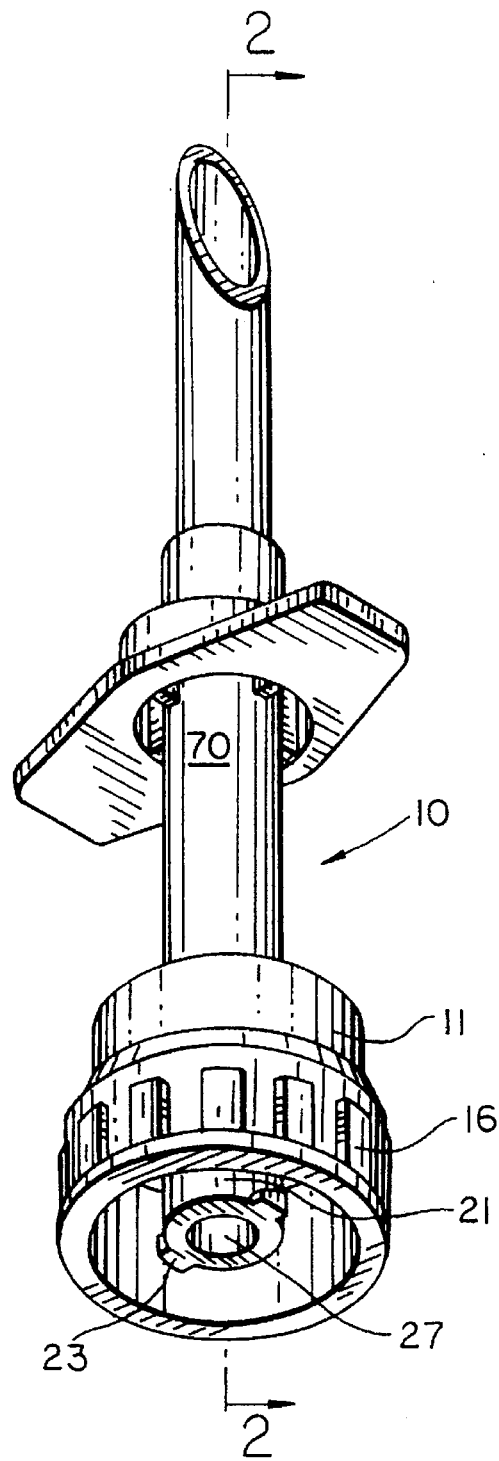
FIG. 2
FIG. 1

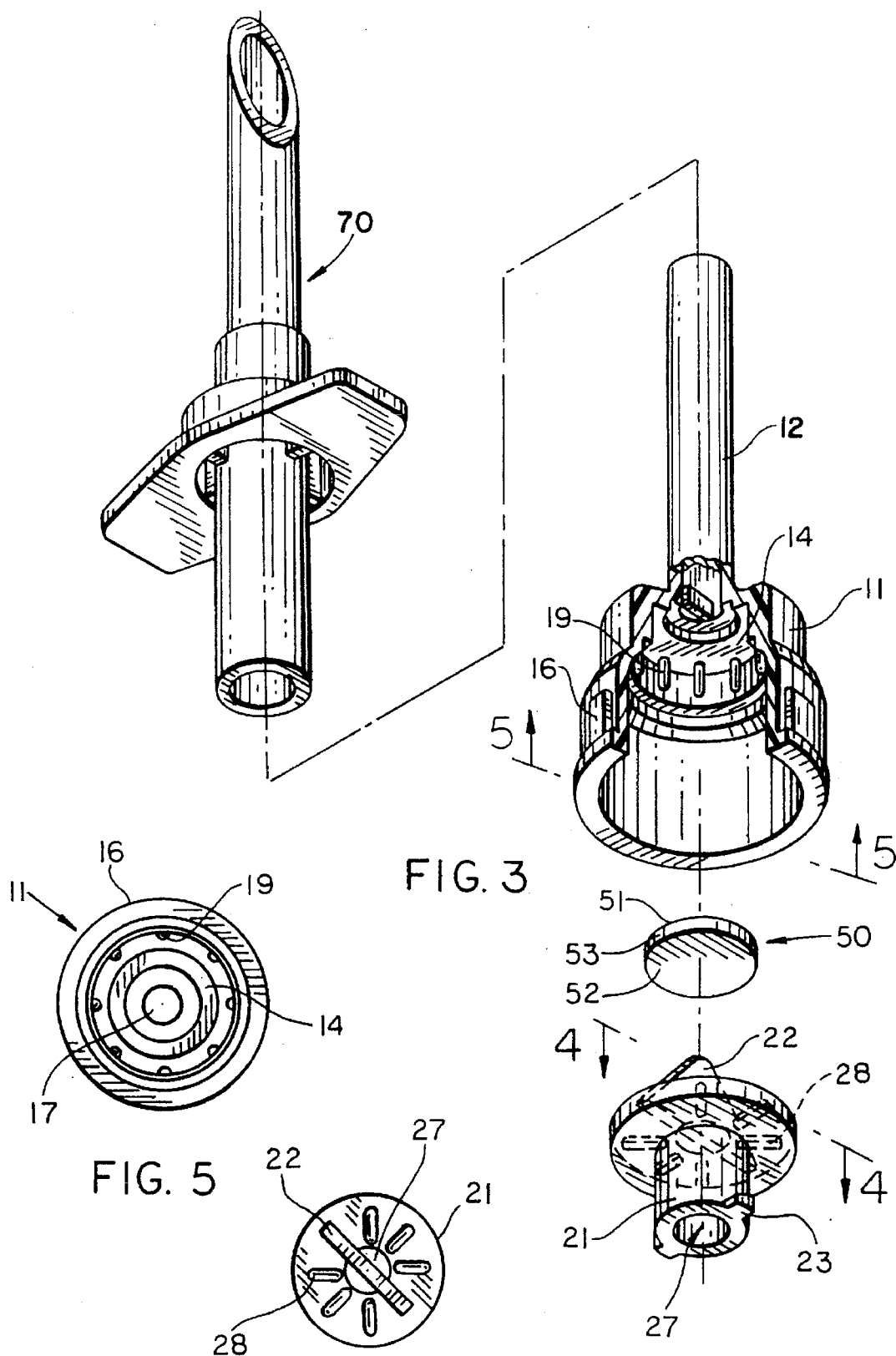

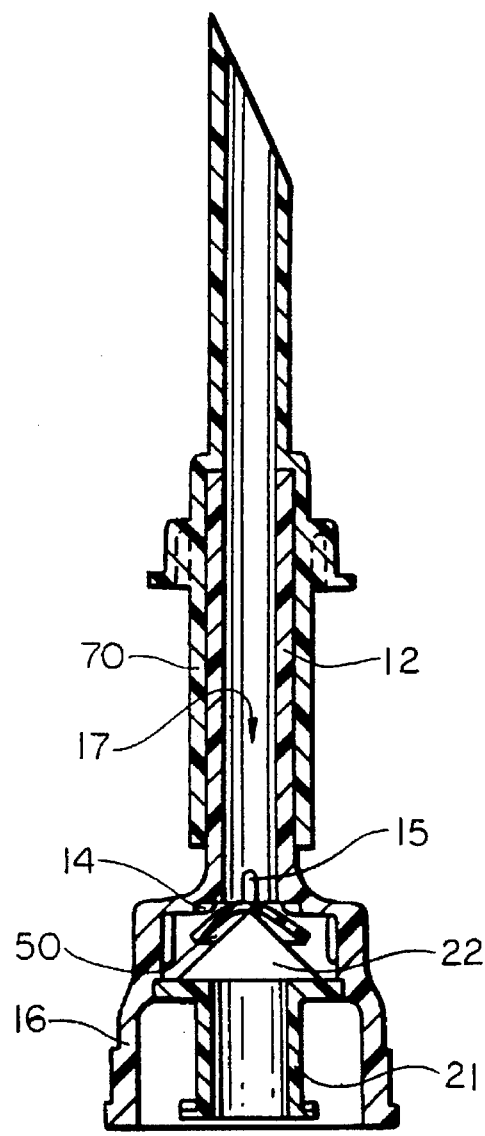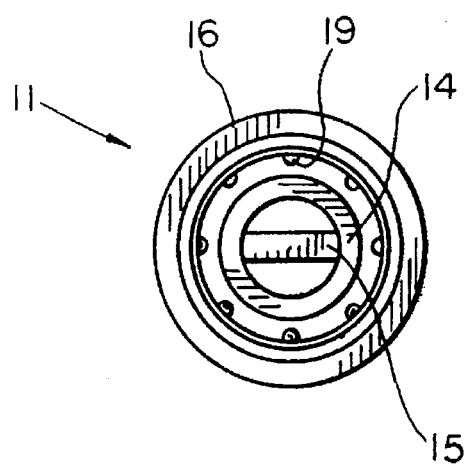
FIG. 6
FIG. 7

5,623,969

NORMALLY CLOSED ASPIRATION VALVE

FIELD OF THE INVENTION

This invention relates generally to backflow check valves for liquid flow systems. More particularly, the present invention comprises a one-way dispensing valve assembly for aspirating fluid from containers.

BACKGROUND OF THE INVENTION

Check valves for fluid administration systems are well known, particularly in the medical field where it is desirable to have a valve which quickly returns to the closed position when flow is reversed in an intravenous system or the like. Conventional backflow check valves are normally closed devices that open only when subjected to an increase in flow pressure. When the pressure is reduced, the valve quickly returns to the closed position. Typical valves are disclosed in U.S. Pat. Nos. 4,246,932, 4,286,628, 4,310,017, 4,369,812 and 4,422,407.

U.S. Pat. No. 4,535,820 also describes a one-way flow valve. This assembly can be used in a system for injecting fluid into a container such as an intravenous fluid bag. The '820 patent teaches a normally closed valve which permits only one-way flow into a container. One cannot remove or withdraw fluid from a container with this device.

U.S. Pat. No. 4,683,916 describes a two-way, normally closed reflux valve which permits both injection and aspiration of fluid into and out of containers. When used with a needleless system, the blunt syringe engages a valve plunger which moves the valve disc and holds it away from the valve seat, permitting flow in both directions depending on the action of the syringe. When the syringe is disconnected, the disc-positioning force is removed and the disc returns to its normally closed position against the valve seat.

In a hospital type environment, medications and/or pharmaceutical solutions are typically stored in large containers at pre-selected concentrations. These containers are frequently located in common areas which are accessible to a large number of health care providers. When administering patient care, individual workers frequently withdraw fluid from these containers to administer or formulate medications and other therapeutic solutions.

Known two-way valves can be used with a piercing device or spike to withdraw fluid from receptacles containing pharmaceutical solutions. But, there are hazards associated with these two-way systems during end-use application. For example, known designs allow medical technicians to withdraw a volume of solution from a container, administer it to a patient and return the unused portion to its original container, possibly causing the introduction of contaminants and infectants. Unused fluid from a syringe which is reintroduced to its container may also alter and/or dilute the original fluid concentration. These disfavored practices are prevented with the valve of the present invention.

Another problem with two way valves is that the contents of a syringe can be accidentally introduced to a container having a different solution, i.e., not the container from which the fluid was originally withdrawn. Under these circumstances, the result could be a harmful, toxic or even fatal mixture of medications or fluids.

To avoid these pitfalls, there is a need in the art for a one-way aspiration valve which allows for withdrawal of fluid from a container, but which does not allow an injection back into the same or different container. The present invention overcomes the problems associated with conventional devices by permitting aspiration only with no possibility of reverse flow in the opposite direction.

OBJECTS OF THE INVENTION

It is an object of the present invention to provide a one-way dispensing valve assembly for aspirating fluid, which allows for withdrawal of fluid from a container, but does not allow flow back into the same or different container.

Another object of the present invention is to provide a one-way aspiration valve which prevents the introduction of contaminants and infectants back into an original receptacle.

A further object of the present invention is to provide a one-way dispensing valve assembly for aspirating fluid which prevents alteration and dilution of the fluid in an original container by preventing the reintroduction of an unused portion of the fluid back into the original container.

Another object is to provide a one-way dispensing valve assembly for aspirating fluid which prevents the introduction of unused portions of the aspirated fluid into an entirely different (wrong) container.

Yet another object of the present invention is to provide a valve assembly having a simple, unitary structure which is easy to manufacture.

These and other objects will become evident from the disclosure provided below.

SUMMARY OF THE INVENTION

The present invention is a normally closed, pressure activated check valve for aspirating fluid from a container without permitting flow back into the container. The valve device is comprised of a hollow, first body element which contains a first passageway, a shoulder or valve seat disposed in its inner wall and a shroud. The device also has a second body element which, in the final assembly, is partially disposed within the first body element substantially proximate to the shoulder. This second body element contains a support member, which may have various configurations, and a second passageway which communicates with the first passageway to permit one-way, aspirating flow through the valve housing.

A flexible valve disc, having top and bottom surfaces and a peripheral edge, is mounted between the first and second body elements so that the disc is partially flexed and a portion of the top surface of the disc forms an annular seal against the shoulder of the first body element. In the closed condition, fluid cannot flow between the first and second passageways.

The device of the present invention is used for aspirating fluid from a container such as an intravenous fluid bag. When a syringe is attached to the second body element and the syringe plunger is withdrawn, a negative pressure drop is created in the second passageway which increases the relative pressure forcing the disc to further flex away from the valve seat (shoulder). Under these conditions, the valve is in the open position and the first passageway of the first body element cooperates with the second passageway of the second body element to permit fluid aspiration from the container into an attached syringe barrel.

When the negative pressure created by the syringe plunger is released, the disc returns to its normally closed position with the top surface of the disc and the shoulder forming an annular seal. When a full or partially full syringe is attached to the dispensing valve assembly, it is impossible to empty the contents of the syringe into a container through the valve. Any positive pressure applied by the syringe plunger will only contribute to a tighter seal between the top surface of the disc and the valve shoulder.

According to another embodiment of this invention, the normally closed aspiration valve has a traverse bar disposed within the first body element. In this embodiment, the top surface of the disc contacts the traverse bar and the bottom surface of the disc engages the support member to prevent displacement of the disc into the first body element.

BRIEF DESCRIPTION OF THE DRAWINGS

FIG. 1 is a perspective view of a device assembled according to the present invention.

FIG. 2 is a cross-sectional view taken generally along line 2—2 in FIG. 1.

FIG. 3 is an exploded perspective view of the present invention.

FIG. 4 is a top plan view taken generally along line 4—4 in FIG. 3.

FIG. 5 is a bottom plan view taken generally along line 5—5 in FIG. 3.

FIG. 6 is a cross-sectional view of a second embodiment of the present invention having a traverse cross bar.

FIG. 7 is a bottom plan view of the embodiment shown in FIG. 6.

DETAILED DESCRIPTION OF THE INVENTION

Figure 8:
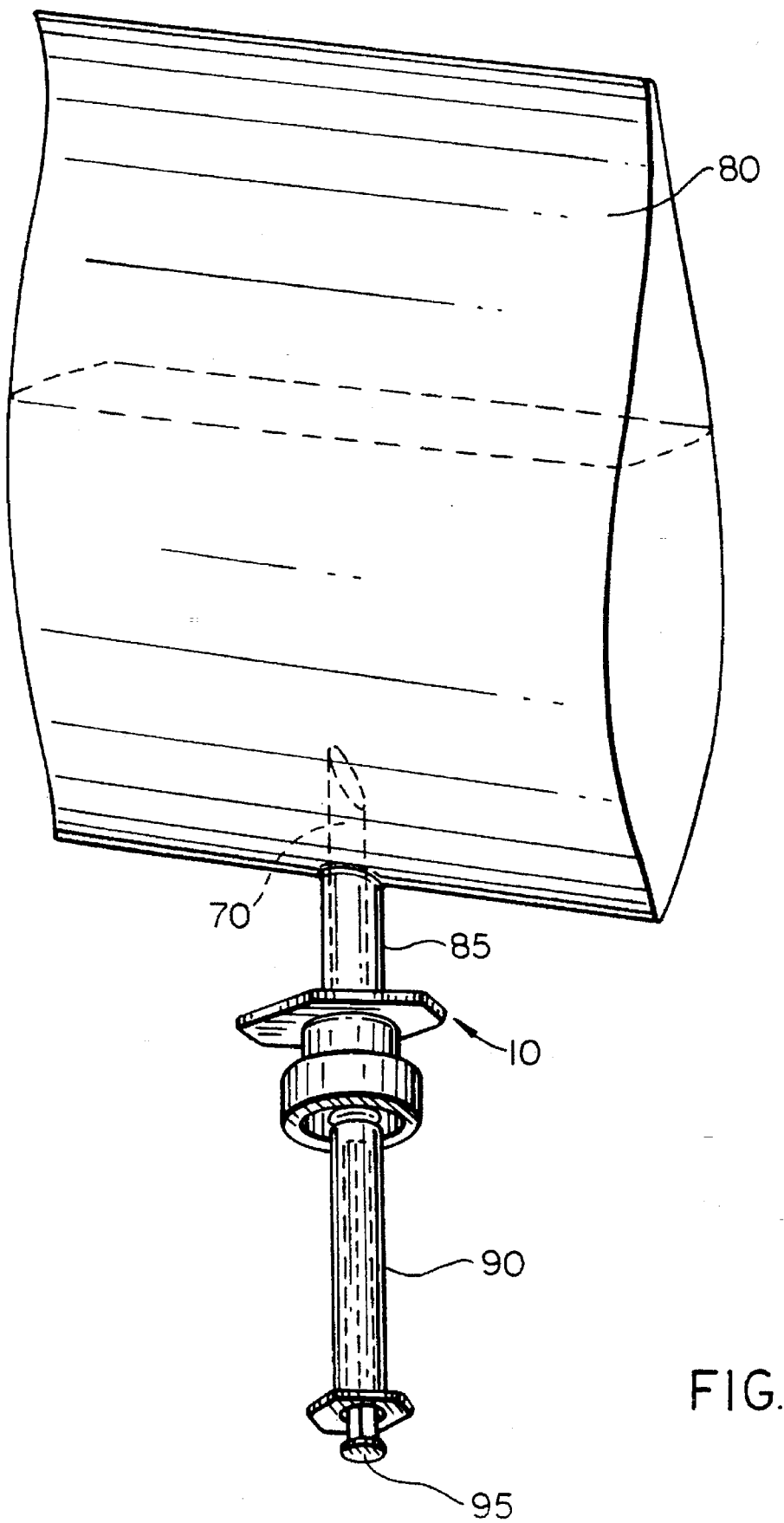
FIG. 8 is a perspective view of a system for aspirating fluid using the valve of the present invention.

Referring to FIGS. 1 and 2, the present invention is generally designated with reference numeral 10. A one-way, normally closed check valve of the present invention generally includes two basic elements. First body element 11 has tubular portion 12, shoulder 14 and shroud 16 which provides a handle for ready access. Second body element 21, having passageway 27 and ears 23, is partially recessed within shroud 16 in the final assembly. The valve housing, comprised of first body element 11 and second body element 21, is illustrated in FIG. 1 along with spike 70.

The cross-sectional view in FIG. 2 shows first body element 11 with enlarged shroud 16 and tubular portion 12 having first passageway 17 therethrough. Tubular portion 12 is shown inserted into spike 70. Second body element 21 is shown recessed within shroud 16 such that second passageway 27 is normally sealed or closed from first passageway 17 by resilient valve disc 50. Resilient valve disc 50 comprises top surface 51, bottom surface 52 and peripheral edge 53 (see FIG. 3). Valve disc 50 can be made from a number of resilient materials, such as silicone elastomer, in a variety of suitable thicknesses.

FIG. 2 shows second body element 21 having support member 22 which is illustrated as a triangular base, but can be any shape which will accommodate bottom surface 52 of disc 50 and help provide a seal between top surface 51 and valve shoulder 14.

In the normally closed position, valve disc 50 is partially flexed by support member 22 against shoulder 14 to form an annular seal. During aspiration, valve disc 50 is further flexed and separated from shoulder 14 by the drop in differential pressure exerted by the pull of a syringe plunger. As valve disc 50 is flexed away from shoulder 14, the annular seal is broken to permit fluid flow from passageway 17 to passageway 27, typically in a downward or lateral direction. When the pulling action of the syringe is stopped, disc 50 returns to its original, normally closed position with top surface 51 in contact with shoulder 14, thereby renewing the seal and preventing flow in either direction, specifically flow from the syringe back into an attached container.

In a preferred embodiment, the top of support member 22 is substantially co-planar with shoulder 14. This spatial relationship creates a seal between support member 22, disc 50 and shoulder 14 for a variety of disc thicknesses.

FIG. 3 shows an exploded perspective view of the present invention, including a partial cutaway of first body element 11. The inner circumferential wall of first body element 11 is provided with a plurality of vertically extending ribs 19 which reduce binding of peripheral edge 53 of valve disc 50 as contained within first body element 11.

Valve disc 50 is illustrated in FIG. 3 as a circular disc in its flat, extended conformation. As seen in connection with FIG. 2, disc 50 is flexible and changes from its flat, extended conformation to the partially flexed position after assembly with other components, most notably support member 22 of second body element 21. FIG. 3 also shows second body element 21 which is comprised of radial support ribs 28 shown with phantom lines. Radial support ribs 28 assure an adequate space for liquid flow about peripheral edge 53 of disc 50 when it is further flexed in the open flow position.

To assemble the valve, sonic welding is preferably used to securely fasten first body element 11 and second body element 21 into a single, integral unit. Suitable methods for sealing first body element 11 and second body element 21 also include the use of adhesives and other conventional means for bonding materials. It is important that the seal be liquid tight to prevent leakage and disassembly without complete destruction of the valve. In like manner, spike 70 is attached to first body element 11 by adhesive or other conventional bonding techniques.

FIG. 4, taken generally along line 4—4 in FIG. 3, shows support member 22 and its relationship to passageway 27. FIG. 4 also shows radial support ribs 28 attached to second body element 21. FIG. 5, taken generally along line 5—5 in FIG. 3, shows the relative positions of shroud 16, vertically extending ribs 19, shoulder 14 and passageway 17 in first body element 11.

FIG. 6 is a cross-sectional view of another embodiment of the present invention having traverse bar 15 which is shown again in FIG. 7 from below. According to this embodiment, the lower surface of bar 15 firmly presses against top surface 51 of disc 50 and bottom surface 52 of disc 50 contacts support member 22. The presence of bar 15 prevents disc 50 from being forced into passageway 17 under excessive pressure when, for example, an end-user inadvertently attempts to empty the fluid contents of a syringe barrel back into a container. Under these circumstances, the syringe pressure would enhance the seal between top surface 51 of disc 50 and shoulder 14; and bar 15 provides added assurance that disc 50 will not be forced into passageway 17.

The opposing pressures provided by bar 15 and support member 22 may operate to form a small indentation on the bottom surface 52 of interdisposed disc 50. This indentation may partially restrain the sideways movement of disc 50. In any event, vertical ribs 19 prevent frictional binding of disc 50 with the inner side wall of first body element 11.

FIG. 8 is a perspective view of container (fluid bag) 80, the device of the present invention 10 and syringe 90. Normally closed aspiration valve 10 has been inserted into bag 80 through end piece 85. Syringe 90 is rotatably connected by ears 23 to normally closed valve 10. As discussed above, when syringe plunger 95 is withdrawn from the barrel a negative pressure drop is created which causes further flexing of disc 50 away from shoulder 14. In this condition, fluid will flow from bag 80 through first and second passageways 17 and 27 into syringe 90. Once the desired amount of fluid has been withdrawn, syringe 90 can be disconnected with its contents ready for patient administration and the like.

This specification is intended to illustrate the principal features of the present invention. Various modifications and alterations may be appreciated based on a review of this disclosure. These changes and additions are intended to be within the scope and spirit of this invention as defined by the following claims.

What is claimed is:

1. A normally closed aspiration valve device comprising:
   a first body element having a first passageway therethrough and a shoulder disposed in an inner wall thereof;
   a second body element having a second passageway therethrough, a support member and a means for syringe attachment, said second body element attached to said first body element; and
   a flexible valve disc having a top surface, said disc mounted between said first and second body elements with said disc partially flexed, said first and second body elements and said disc forming a one-way valve, wherein said top surface of sale disc forms an annular seal with said shoulder preventing flow of a fluid between said first and second passageways, and wherein a fluid pressure drop in said second passageway increases the relative pressure in said first passageway such that said disc is further flexed away from said shoulder and allows fluid from said first passageway into said second passageway.

2. The valve device of claim 1, wherein
   said first body element has a shroud and a tubular portion which forms said first passageway; and
   said second body element is recessed within said shroud such that when said device is in said normally closed position, said disc is partially flexed by said support member against said shoulder forming said annular seal.

3. The valve device of claim 2, wherein said tubular portion is inserted into a spike for aspiration from a container.

4. The valve device of claim 2, wherein said disc is further flexed during aspiration and said first surface of said disc is pulled away from said shoulder by the drop in differential pressure exerted during said aspiration terminating said annular seal thereby.

5. The valve device of claim 4, wherein said first surface of said disc returns to said shoulder renewing said annular seal and preventing reversal of flow when said drop in differential pressure is terminated.

6. The valve device of claim 1, wherein said second body element is comprised of a plurality of radial support rib means for assuring liquid flow about said peripheral edge of said disc when said disc is further flexed in an open flow position.

7. The valve device of claim 1, wherein said support member is substantially co-planar with said shoulder thereby creating said annular seal between said support member and said shoulder.

8. A valve device comprising:
   a first body element having a first passageway therethrough and a shoulder disposed in an inner wall thereof;
   a second body element having a second passageway therethrough, a support member and a means for syringe attachment, said second body element attached to said first body element; and
   a flexible valve disc having a top surface, said disc mounted between said first and second body elements with said disc partially flexed, said first and second body elements and said disc forming a one-way valve, wherein said top surface of said disc forms an annular seal with said shoulder preventing flow of a fluid between said first and second passageways, and wherein a fluid pressure drop in said second passageway increases the relative pressure in said first passageway such that said disc is further flexed away from said shoulder and allows fluid from said first passageway into said second passageway, and wherein said first body element has a traverse bar having a lower surface which presses said disc against said support member.

9. The valve device of claim 8, wherein said lower surface of said traverse bar presses said top surface of said disc to bias said disc against said support member.

10. The valve device of claim 9, wherein
    said first body element has a shroud and a tubular portion which forms said first passageway; and
    said second body element is recessed within said shroud such that when said device is in said normally closed position, said disc is partially flexed by said support member against said shoulder forming said annular seal.

11. The valve device of claim 10, wherein said tubular portion is inserted into a spike for aspiration from a container.

12. The valve device of claim 10, wherein said disc is further flexed during aspiration and said first surface of said disc is pulled away from said shoulder by the drop in differential pressure exerted during said aspiration terminating said annular seal thereby.

13. The valve device of claim 12, wherein said first surface of said disc returns to said shoulder renewing said annular seal and preventing reversal of flow when said drop in differential pressure is terminated.

14. The valve device of claim 8, wherein said second body element is comprised of a plurality of radial support rib means for assuring liquid flow about said peripheral edge of said disc when said disc is further flexed in an open flow position.

15. The valve device of claim 8, wherein said support member is substantially co-planar with said shoulder thereby creating said annular seal between said support member and said shoulder.

16. A system for aspirating fluids from containers, comprising:
    a. at least one fluid container;
    b. at least one piercing spike;
    c. at least one valve device comprising a first body element having a first passageway therethrough and a shoulder disposed in an inner wall thereof; a second body element having a second passageway therethrough, a support member and a means for syringe attachment, said second body element second body element attached to said first body element; and a flexible valve disc having a top surface, said disc mounted between said first and second body elements with said disc partially flexed, said first and second body elements and said disc forming a one-way valve, wherein said top surface of said disc forms an annular seal with said shoulder preventing flow of a fluid between said first and second passageways; and d. at least one needlefree syringe attached to said valve device at said means for syringe attachment for creating a fluid pressure drop in said second passageway which increases the relative pressure in said first passageway such that said disc is further flexed away from said shoulder end allows fluid from said container to flow through said first and second passageways into said needlefree syringe.

17. The system for aspirating fluid of claim 16 further comprising a traverse bar within said first body element, said traverse bar having a lower surface which presses against said top surface of said disc to bias said disc against said support member.

* * * * *